United States Patent [19]

Bressman et al.

[11] Patent Number: 5,620,323
[45] Date of Patent: Apr. 15, 1997

[54] DENTAL RESTORATION STRUCTURE

[76] Inventors: Robert A. Bressman, 9631 Gross Point Rd., Skokie, Ill. 60076; Daniel Megert, Horeastrasse 17, 3186 Duedingen, Switzerland

[21] Appl. No.: 293,560

[22] Filed: Aug. 22, 1994

[51] Int. Cl.$^6$ .................................................. A61C 8/00
[52] U.S. Cl. .......................................... 433/174; 433/211
[58] Field of Search ................................... 433/172, 173, 433/174, 175, 176, 201.1, 218–221, 222.1, 202.1, 204, 205, 211

[56] References Cited

U.S. PATENT DOCUMENTS

| | | | |
|---|---|---|---|
| 3,579,831 | 5/1971 | Stevens et al. | 433/173 |
| 4,932,868 | 6/1990 | Linkow et al. | 433/174 |
| 5,071,345 | 12/1991 | Rosen | 433/173 X |
| 5,082,445 | 1/1992 | Singer | 433/169 |
| 5,106,299 | 4/1992 | Ghalili | 433/172 |
| 5,199,873 | 4/1993 | Schulte et al. | 433/174 |
| 5,431,567 | 7/1995 | Daftery | 433/172 |
| 5,478,237 | 12/1995 | Ishizawa | 433/201.1 |

FOREIGN PATENT DOCUMENTS

| | | |
|---|---|---|
| 3241963 | 4/1984 | Germany. |
| 8903050 | 6/1989 | Germany. |
| 2063680 | 6/1981 | United Kingdom. |
| 9306786 | 4/1993 | WIPO. |

OTHER PUBLICATIONS

Product Literature for CAPTEK™ Materials.
Ledermann et al, *Schweiz Monatsschr. Zahnmed.*, vol. 101 (5), pp. 611–617 (1991).

*Primary Examiner*—Christopher A. Bennett
*Attorney, Agent, or Firm*—Timothy R. Kroboth

[57] ABSTRACT

A self-cutting implant anchorable in a jawbone is provided. In a preferred embodiment, cutting teeth of the implant include a non-cutting edge opposite to a cutting leading edge. Also provided is a crown structure formed from a collar including aligned bores. In addition, a process for making the crown structure is provided.

9 Claims, 2 Drawing Sheets

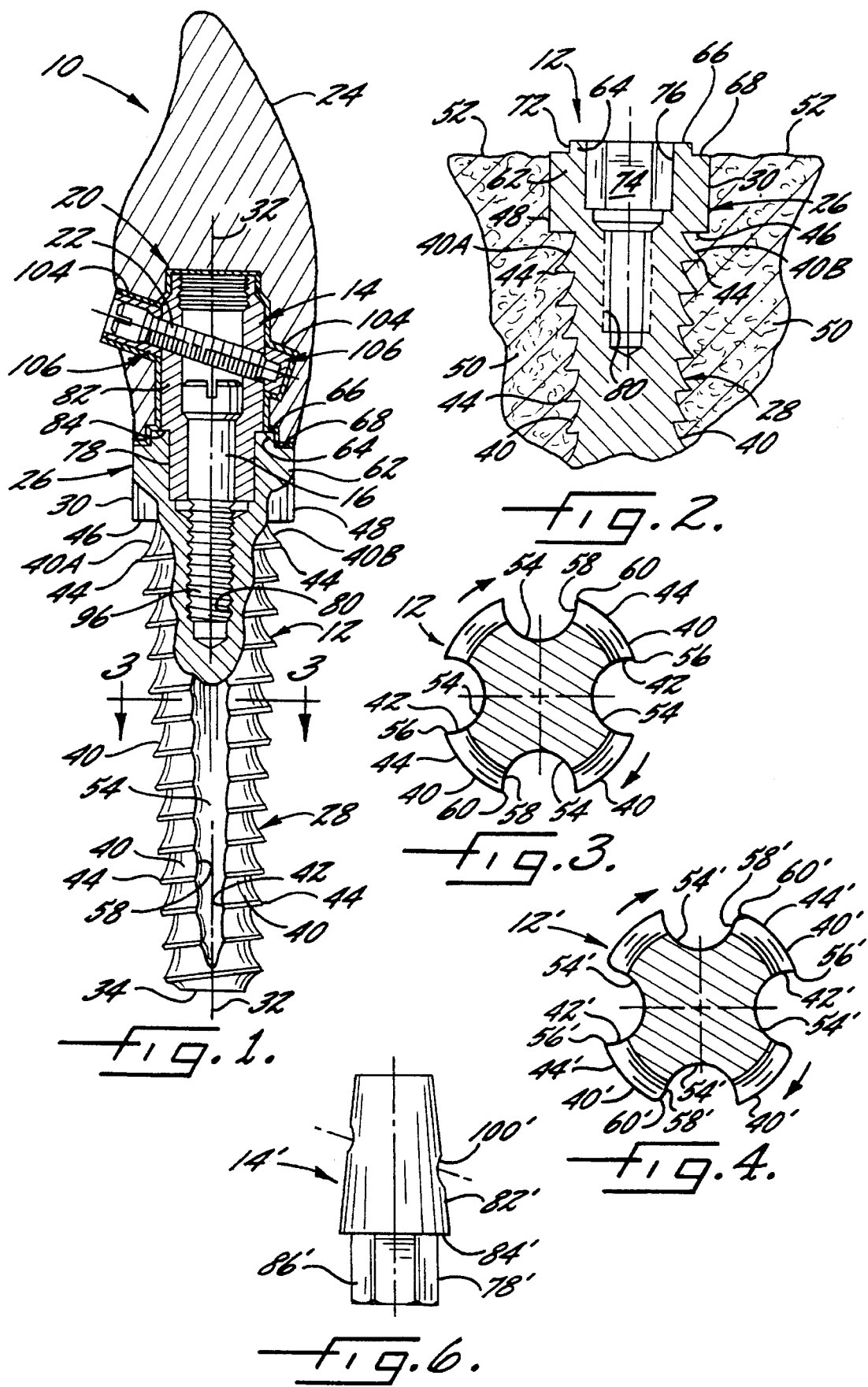

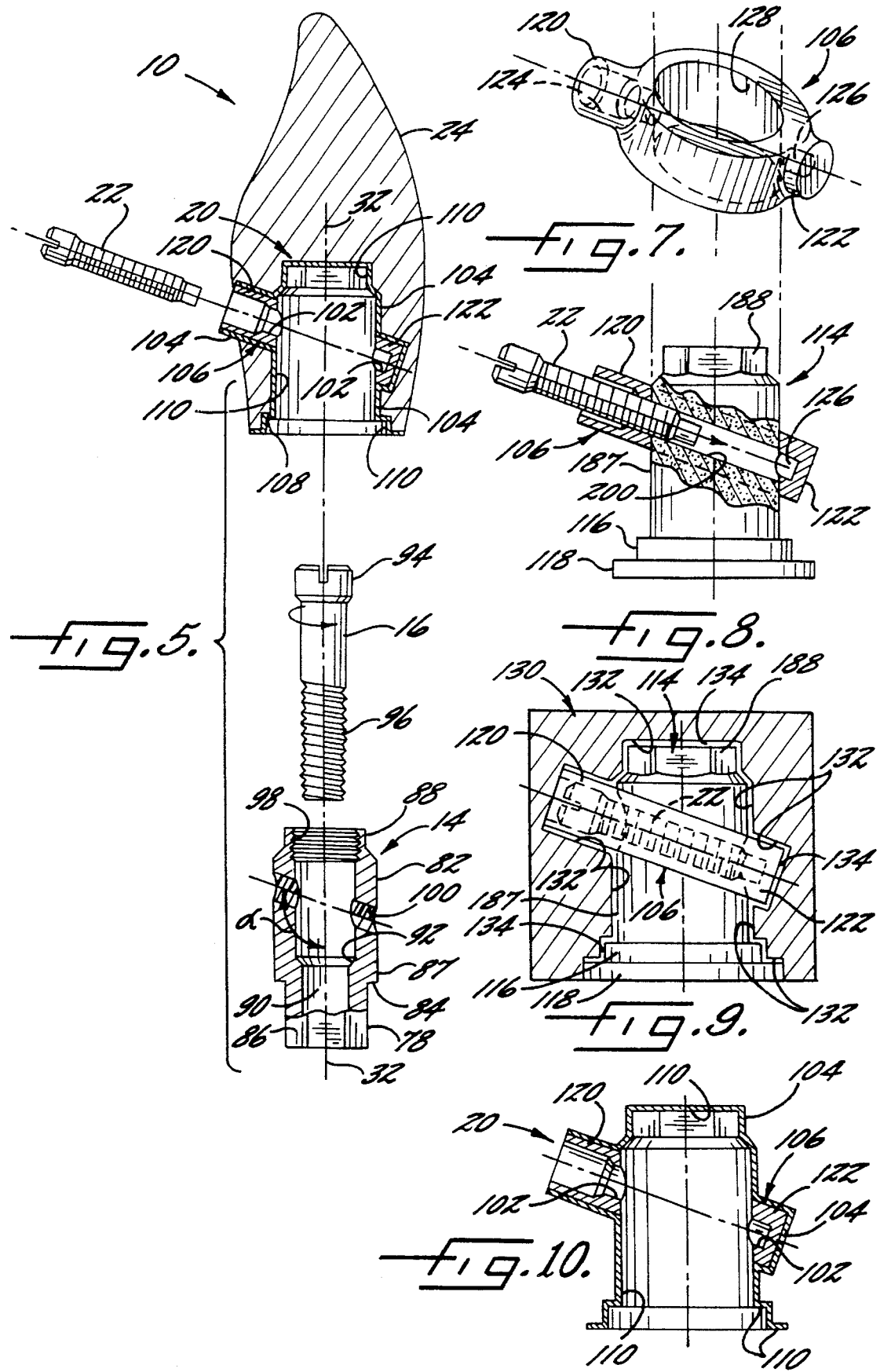

DENTAL RESTORATION STRUCTURE

FIELD OF THE INVENTION

This invention relates to dental implants, in particular to self-cutting implants, and to associated dental restoration structures.

BACKGROUND OF THE INVENTION

Dental restoration structures are known as illustrated by U.S. Pat. Nos. 5,199,873 to Schulte et al, and 4,932,868 to Linkow et al, and by Ledermann et al, *Schweiz Monatsschr. Zahnmed.*, vol. 101 (5), pp. 611–617 (1991). In this respect, prior workers have made a considerable effort to provide an improved implant. Implant failure can lead to significant destruction of alveolar bone. It has been found through prior effort that self-tapping implants are advantageous. Also found to be beneficial are single body implants.

Commercial implants include the self-tapping, single body implant described in the Ledermann et al publication. This implant has a tapered profile and longitudinal grooves that form cutting teeth. An interior cavity includes a hexagonally-shaped, upper portion for receiving an abutment member having a longitudinal bore, and a lower portion for engaging threads of a screw for securing the abutment member to the implant. The abutment member is used to connect the implant to a crown structure.

However, pressure-induced bone resorption or necrosis may occur with the implant. Additionally, when the abutment member is secured to the implant by rotation of the abutment screw, undesirable additional cutting of bone or detachment may occur due to engagement of the implant cutting teeth.

A crown structure often used with the implant of the Ledermann et al publication, includes a transverse inclined bore for coaxial alignment with a corresponding transverse inclined bore of the abutment member. In this case, the crown structure is attached to a crown end of the abutment by means of a transverse screw threaded into the aligned bores. The bore in the crown structure may advantageously be slightly higher than the bore in the abutment to produce a press fit of the crown to the implant when the bores are aligned by use of the screw.

Commercial crown structures for use with implants are typically prepared from a block of gold of about 2 to 3 mm thickness. These crown structures are formed to have an appropriate interior shape by removal of gold from the gold block. The process is labor-intensive and costly.

Accordingly, there continues to be a need for improved dental implants and for less expensive dental crowns for use with implants. Likewise, there is a need for a process for making less expensive dental crowns for use with implants.

SUMMARY OF THE INVENTION

In accordance with the present invention, a dental restoration structure including a novel self-cutting implant anchorable in a jawbone, is provided. Beneficially, the implant includes a generally cylindrical neck, and a tapered, thread cutting portion that includes cutting teeth. Individual cutting teeth include a cutting leading edge, and a peripheral edge for anchoring the implant. Advantageously, a bottom wall of the implant neck is generally perpendicular to a peripheral wall of the neck to provide a stepped joining of the neck and the thread cutting portion. In addition, the peripheral edges of the cutting teeth adjacent the implant neck, are beneficially stepped in from a plane formed by the peripheral wall. As a result, depth of the implant is limited and pressure-induced bone resorption or necrosis is reduced.

Also provided is a dental restoration structure including a self-cutting implant anchorable in a jawbone, a crown/tooth structure, means for connecting the crown/tooth structure to the implant, and means for securing the connecting means to the implant. In this embodiment of the invention, the implant includes a thread cutting portion including cutting teeth each including a cutting leading edge, and the implant has a thread direction defined by the cutting teeth. In addition, the implant is provided with a cavity for receiving an implant end of the connecting means and for engagement by a threaded root end of the securing means; and the threaded root end has a thread direction advantageously opposite to the implant thread direction. As a result, engagement of the cutting edges of the cutting teeth is prevented when the securing means is rotated to secure the abutment within the implant.

Beneficially, individual cutting teeth may also include a non-cutting edge opposite to the cutting leading edge. As a result, cutting action of the cutting teeth opposite to the original direction of implanting, is prevented when the abutment is secured using the reverse-threaded screw.

Also provided is a dental restoration structure including a novel crown structure. Advantageously, the crown structure includes a layer to which a tooth structure is bonded, and an integral collar including aligned bores and in bonding contact with the layer. Suitably, the layer overlays the collar.

The crown structure has a mating interior shape and dimensions for fitting over a crown end of means for connecting the crown structure to an implant. Beneficially, the aligned bores of the collar of the crown structure form an inclined bore for coaxial alignment with a correspondingly inclined, transverse bore of the crown end of the connecting means.

Also provided is a process for making a novel crown structure in accordance with the invention. In accordance with the process, a collar including aligned bores, is disposed around a model of the crown end of the connecting means. The model has an inclined transverse bore correspondingly inclined as that of the crown end of the connecting means. The bores of the collar and model are aligned, and a member is inserted into the aligned bores to secure the collar onto a proper location of the model, which typically has a generally cylindrical, crown end.

Then, the exterior of the resulting structure is overlayed with a material suitable for forming the crown layer, such that a layer generally corresponding to the exterior shape is formed. After further processing appropriate to the material selected, the crown structure is provided.

In the detailed description of the invention that follows, there are essentially described only preferred embodiments of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWINGS

Reference is now made to the accompanying drawing, which forms a part of the specification of the present invention.

FIG. 1 is a partial cross-sectional view of a preferred dental restoration structure in accordance with the present invention;

FIG. 2 is an enlarged, cross-sectional view of a portion of the implant of the dental restoration structure of FIG. 1, implanted in a bone mass;

FIG. 3 is a cross-sectional view of the implant taken substantially along line 3—3 of FIG. 1;

FIG. 4 is a cross-sectional view similar to FIG. 3, showing alternative cutting teeth;

FIG. 5 is an exploded, partial cross-sectional view of the crown/tooth structure, transverse screw, abutment screw, and abutment of the dental restoration structure of FIG. 1;

FIG. 6 is a perspective view of an alternative abutment;

FIG. 7 is a perspective view of a collar useful in making the crown structure of FIG. 1;

FIGS. 8 and 9 depict steps in a process for making the crown structure of FIG. 1; and FIG. 10 is an enlarged, cross-sectional view of the crown structure of FIG. 1.

DETAILED DESCRIPTION OF THE INVENTION

As indicated above, the present invention relates to an advantageous dental restoration structure including a novel thread cutting implant. The invention further relates to a novel crown structure and process for making the crown structure. This dental restoration structure is useful in the maxilla and mandible for individual crowns, tissue bars, constructions, overdentures and complete implant-borne bridges.

Referring to FIG. 1, a preferred dental restoration structure 10 in accordance with the present invention, includes a self-cutting implant 12 anchorable in a jawbone, a connecting member or abutment 14 fastenable to the implant by an abutment screw 16, a crown structure 20 securable to the abutment by a transverse screw 22, and a tooth structure 24 overlaying and bonded to the crown structure.

Advantageously, preferred implant 12 includes a generally cylindrical neck 26 and a tapered, thread cutting portion 28. Neck 26 has a peripheral wall 30 that is generally parallel to a longitudinal axis 32 of the implant and dental restoration structure, whereas thread cutting portion 28 tapers in the direction of a tip 34, which is preferably blunt.

Preferably, the peripheral wall of the implant neck is smooth, and very preferably the wall is polished. The lack of threads on the peripheral wall facilitates cleaning. Moreover, inflammation-free mucosa integration and the formation of a junctional epithelium may result. A typical length of the peripheral wall ranges from about 1 mm to 3 mm.

The thread cutting portion of the implant includes a plurality of self-tapping threads or cutting teeth 40. This feature beneficially avoids the need to tap threads into an implant bed before insertion of the implant. Referring also to FIG. 3, which indicates the direction of rotation of the implant and cutting teeth, the cutting teeth include a leading edge 42 for cutting into the jawbone of a patient, and a peripheral edge 44 for providing an anchoring action.

Preferably, the thread cutting portion of the implant is slightly roughened to promote osseointegration. A suitable roughening will typically be about 50 to 100 nm. Roughening may be provided by, for instance, anodizing to provide a ceramic-like surface. This slightly roughened surface combined with the use of self-tapping, cutting teeth to cut the final bed, promotes exceptional osseointegration.

The implant is advantageously made of pure titanium having a surface layer of titanium dioxide (rutile). Accordingly, peri-implant soft tissue and bone do not directly contact titanium metal.

With reference to FIGS. 1 and 2, the implant advantageously has a stepped profile. In particular, a bottom wall 46 of the implant neck is generally perpendicular with respect to the peripheral wall of the generally cylindrical neck to provide a stepped joining of the neck and thread cutting portion 28. This advantageous structure may be contrasted to the bottom wall of the cylindrical neck of the Linkow et al implant, which provides a tapered joining of the neck and threaded portion thereof. In addition, in the present invention, a root end 48 of the implant neck is of a diameter greater than any diameter of the tapered cutting portion. More particularly, the peripheral edge of each of the cutting teeth adjacent the implant neck, is stepped in from the plane of the peripheral wall of root end 48. These cutting teeth include the cutting teeth designated 40A,40B in FIGS. 1 and 2. This beneficial structure is in contrast to the corresponding threads of the Schulte et al implant, which extend beyond the plane of the peripheral wall of the root end of the cylindrical neck thereof. As a result of these features, a depth-limiting step or ledge is formed for limiting depth of an implant, so as to reduce pressure-induced bone resorption or necrosis. A typical depth is illustrated in FIG. 2, in which bone structure is designated 50 and the crest of bone is designated 52.

An especially suitable angle of taper of the thread cutting portion of the implant is about 5°. Other angles of taper may, of course, be used. As indicated in FIG. 1, the thread cutting portion is continuously tapered to tip 34. As a result, a cutting action is provided along its entire length. This advantageous implant structure may be contrasted with the stepped, tapering implant structure of Schulte et al, in which the diameters of successive steps decrease toward the implant tip.

Referring to FIGS. 1 and 3, grooves 54 in the thread cutting portion of the implant provide cutting teeth 40 each having cutting leading edge 42, and in addition increase the implant surface area, which assists force distribution. Beneficially, grooves 54 extend from near blunt tip 34 into root end 48 of the implant neck. Disposed lateral to grooves 54 are short grooves (not shown), also longitudinally aligned, that extend from tip 34 approximately to root ends of grooves 54. In combination with grooves 54, these grooves provide cutting teeth the length of the tapered portion of the implant, and provide for channeling of bone fragments from the borehole. However, grooves 54 may not extend so far into the implant neck as to allow incursion of food and bacteria. Longitudinal alignment of a groove with longitudinal axis 32 results in cutting leading edges 42 of the groove generally forming a common plane.

With continued reference to FIG. 3, cutting teeth 40 each include a point 56 joining leading edge 42 to peripheral edge 44. In addition, each cutting tooth includes an edge 58 opposite to leading edge 42, and joined to peripheral edge 44 by a pointed junction 60. Opposite edge 58 may be, like the leading edge, sharp for a cutting action.

Alternatively, referring to FIG. 4, an implant 12' may beneficially include cutting teeth 40', which have a non-cutting edge 58' opposite to a leading edge 42' and a peripheral edge 44'. Consistent therewith, opposite edge 58' may be blunt or dull, and the peripheral edge may be joined to opposite edge 58' by a rounded junction 60'.

With reference again to FIGS. 1 and 2, a crown end 62 of the implant neck includes an annular raised step 64 of smaller diameter than the diameter of the root end of the neck. Surface 66 of the raised step and surface 68 of the crown end function as bearing surfaces. More particularly, generally horizontal surface 68 serves as a bearing surface for crown/tooth structure 20,24; and generally horizontal surface 66 of the raised step functions as a bearing surface in addition for abutment 14. Joining surfaces 66,68 is a peripheral wall 72, indicated in FIG. 2, of the annular raised step 64.

Referring particularly to FIG. 2, a recess or cavity 74 in the interior of the implant includes a portion 76 for receiving an implant end 78 of abutment 14. Preferably, portion 76 is provided with a shape or configuration for preventing rotation of the abutment with respect to the implant. Any suitable anti-rotation shape may be used. Portion 76 may also serve to receive an inserted tool to enable a torque to be exerted about longitudinal axis 32 of the implant during implantation. Toward the root end of the implant, cavity 74 includes a lower portion 80 of smaller diameter than portion 76, for engaging threads of abutment screw 16, as shown in FIG. 1.

With reference particularly to FIG. 5, abutment 14, which serves to couple the crown/tooth structure to the implant, has a stepped exterior profile. More particularly, implant end 78 of the abutment is of smaller cross-section than an adjoining crown end 82 thereof, and a seating surface 84 joins implant end 78 and crown end 82. As shown in FIG. 1, seating surface 84 bears upon surface 66 of raised step 64 of the implant.

Implant end 78 of the abutment preferably has a locking peripheral surface 86 for engaging a mating surface in portion 76 of implant cavity 74, so as to secure the abutment against rotation with respect to the implant. As may be understood, cooperation of the lateral surfaces of the implant end of the abutment with mating surfaces of the implant cavity results in an anti-rotational lock.

Crown end 82 of the abutment has a generally cylindrical, peripheral wall 87. Crown end 82 tapers to a boss 88, preferably having a hexagonal external shape for preventing rotation of the crown/tooth structure with respect to the abutment.

The interior of the abutment includes a longitudinal bore 90 for receiving abutment screw 16. The longitudinal bore has an annular shoulder 92 for engagement by a slotted head 94 of connecting screw 16. The abutment is fixedly joined to the implant by means of the abutment screw, which has a threaded root end 96 for engaging lower portion 80 of the implant cavity.

As shown in FIGS. 1, 3 and 5, the direction of the threads of root end 96 of screw 16 is opposite to the direction of the cutting teeth of the implant. This highly beneficial feature prevents engagement of cutting edges 42 of the cutting teeth during tightening of connecting screw 16. Additionally, in cooperation with cutting teeth having non-cutting edges opposite to cutting edges, as exemplified in FIG. 4, this feature prevents a cutting action of the cutting teeth opposite to the original direction of implanting, during tightening of screw 16. As may be understood, instead of a clockwise threading of the implant and a counterclockwise threading of the abutment screw, as shown in the drawing, the threading of the implant and abutment screw may be reversed.

The longitudinal bore of the abutment suitably may include a threaded portion 98 at the crown end of the abutment. When the abutment is secured in place, the longitudinal bore thereof is coaxial with longitudinal axis 2 of the implant and dental restoration structure.

Referring particularly to FIG. 5 again, the abutment further advantageously includes a transverse bore 100 aligned at an obtuse angle e to longitudinal axis 32. Beneficially, this angle may be about 120°. Transverse bore 100 is preferably threaded for engagement of transverse screw 22. As will become understood, the transverse bore, transverse screw and a corresponding bore 102 of crown structure 20 advantageously cooperate to bias the crown/tooth structure against bearing surfaces 66,68 of the crown end of the implant neck. In this way, tight, gap-free contact is provided.

With reference to FIG. 6, an alternative abutment 14' is shown for use with a dental bridge. As may be seen, a crown end 82' of abutment 14' has a conical shape rather than the cylindrical shape of crown end 82 of abutment 14, and lacks a boss. Otherwise, generally speaking, abutment 14' includes the structural features described for abutment 14, including a transverse bore 100'. Accordingly, corresponding numbers are used to designate corresponding features.

As may be understood, other connecting members suitable for connecting an implant in accordance with the present invention, with conventional attachable dental structures may be used.

The novel crown structure of the present invention is now described. Referring again to FIG. 5, and in addition to FIGS. 7 and 10, a preferred crown structure 20 in accordance with the present invention, includes a layer 104 to which tooth structure 24 is bonded, and an integral collar 106 to which layer 104 is bonded. With particular reference to FIGS. 5 and 10, layer 104 may, as shown therein, overlay or partially surround collar 106. When layer 104 overlays the collar, it is not necessary for the collar to be made of a material bondable to porcelain or other tooth-colored restoration material. However, in any event, layer 104 should be of such a material or should be overlayed by such a material. It is well known to use gold for bonding porcelain. Accordingly, if desired, layer 104 and the collar may be gold or a suitable alloy.

A particularly useful material for layer 104 is a composite metal alloy comprised of about 88% gold and about 9% platinum group metals, commercially available under the trademark CAPTEK. When fired, a layer of this alloy is beneficially provided with a three-dimensional network of capillaries, and is highly dense with exceptional strength. When this type of material is used, layer 104 may advantageously have a thickness of about 0.3 to 0.5 mm. It will be understood that the thickness of layer 104 may vary depending upon the material selected to form the layer, with material providing a relatively stronger layer typically requiring relatively less thickness. In this respect, impact, load and fatigue strength are important considerations. Because, generally speaking, a relatively thinner layer is relatively more cost-effective, layer 104 will usually be as thin as practicable.

Collar 106 of crown structure 20 includes bore 102 for receiving transverse screw 22. Bore 102 is inclined at an obtuse angle to longitudinal axis 32 corresponding to the angle of the transverse bore of the abutment to the longitudinal axis. Moreover, bore 102 is disposed for coaxial alignment with the transverse bore of the abutment when the crown structure is secured to the abutment by the transverse screw. However, to provide gap free, biased contact, the path of bore 102 is preferably slightly further from a wall 108 of the crown structure than the path of the transverse bore is from seating surface 84 of the abutment. Alignment of the paths is achieved by use of the transverse screw. This feature also beneficially exerts pressure against the inserted transverse screw to prevent its loosening. Suitably, to this end, there may be an about 0.05 mm difference between the locations of these paths.

Referring particularly to FIGS. 5 and 10, the crown structure advantageously has a mating interior shape and dimensions 110 for fitting over crown end 82 of the abutment, as well as over surfaces 66,68 and peripheral wall 72 of the crown end of the implant neck.

A suitable process for manufacture of crown structure 20 is now described with reference to FIGS. 7 to 10. Collar 106 is slipped over a model 114 of abutment 14 so as to surround a generally cylindrical, peripheral wall 187 of the model. As may be understood from the preceding description, the model advantageously has an inclined transverse bore 200 located slightly higher than inclined transverse bore 100 of abutment 14. Otherwise, the model corresponds to the exterior of the crown end 82 of abutment 14. Accordingly, corresponding numbers are used to designate corresponding features. However, in addition, the model includes annular steps 116,118, of which step 116 corresponds to annular raised step 64 of the implant. The model, typically made of gypsum or plaster, is prepared by a conventional molding technique.

Collar 106 includes bosses 120,122, which respectively include bores 124,126, which are aligned to form bore 102 for receiving transverse screw 22. Bore 126 is preferably a blind bore. The collar further includes an interior wall 128 having a shape and dimensions that mate with peripheral wall 187 of the model at an angle appropriate for coaxially aligning bore 102 of the collar with transverse bore 200 of the model. Transverse screw 22 is used to secure the collar to an appropriate location on the model for alignment of the bores, thereby forming the structure of FIG. 8.

Thereafter, the structure of FIG. 8 is placed in a press former 130 having an interior shape defined by an inner wall 132, and generally corresponding to the exterior shape of the structure of FIG. 8. Inner wall 132 is spaced from the exterior of the structure of FIG. 8 by a distance appropriate to form a gap 134 that provides layer 104 of corresponding thickness. Then, the material for forming layer 104 is added to the press former. After the material has hardened, the press former is removed and layer 104 is processed appropriately.

In the case of a CAPTEK material, a press former is not necessary. Rather, a layer of the CAPTEK material may be applied over the exterior of the structure of FIG. 8 and formed to the exterior shape thereof. Thereafter, heat is applied in accordance with the CAPTEK technique.

Removal of the transverse screw precedes removal of the model so as to provide the crown structure of FIG. 10. The crown structure is now ready for conventional porcelain to crown bonding technique.

As may be understood, crown structure 20 is useful with other dental implants. To this end, the abutment may be modified as appropriate.

The implant bed is typically prepared using drill bits of increasing diameter for making a pilot hole. The pilot hole is provided with a cylindrical upper end for receiving the implant neck, and a tapered root end for receiving the tapered, threaded portion of the implant.

After the implant bed has been prepared, implant 12 is inserted into the pilot hole and slowly rotated into the osseous bed in a clockwise direction. At a suitable time interval after implantation, the implant end of the abutment is firmly fixed in the implant cavity using abutment screw 16, which is advantageously rotated in a counterclockwise direction. Thereafter, the crown structure with its porcelain bake is seated over the crown end of the abutment, so that bore 102 of the crown structure and transverse bore 100 of the abutment are in approximate coaxial alignment. Then, transverse screw 22 is inserted into bore 102 and through transverse bore 100 to force bores 102,100 into alignment and thereby seat the crown/porcelain structure firmly against bearing surfaces 66,68 of the implant.

The present invention may be carried out with various modifications without departing from the spirit or essential attributes thereof, and accordingly, reference should be made to the appended claims, rather than to the foregoing specification as indicating the scope of the invention.

We claim:

1. A dental restoration structure comprising an implant anchorable in a jawbone, and means for securing to said implant connecting means for connecting a crown/tooth structure to said implant, said securing means comprising a threaded root end; wherein said implant comprises a neck portion having a cylindrical peripheral wall, and a tapered, thread cutting portion having generally longitudinally disposed grooves providing cutting teeth comprising a cutting leading edge defining a first thread direction and also providing opposite to said leading edge, a non-cutting edge upon said securing means being rotated opposite to said first thread direction to secure said connecting means, wherein said thread cutting portion further comprises a tip and has a peripheral edge defined by peripheral edges of said cutting teeth, wherein said cutting portion peripheral edge adjacent said neck portion is stepped in from said peripheral wall of said neck portion, wherein said thread cutting portion is tapered toward said tip, and wherein said implant comprises a threaded cavity for receiving said threaded root end of said securing means, and said threaded cavity has a thread direction opposite to said first thread direction.

2. The dental restoration structure of claim 1, wherein said thread cutting portion continuously tapers to said tip.

3. The dental restoration structure of claim 1, wherein said grooves extend from said tip into a root end of said implant neck.

4. The dental restoration structure of claim 1, wherein a bottom wall of said neck portion is disposed generally perpendicular to said cylindrical peripheral wall.

5. The dental restoration structure of claim 1, wherein said non-cutting edge is a blunt edge.

6. The dental restoration structure of claim 1, wherein said cutting teeth further comprise a peripheral edge joined to said non-cutting edge by a rounded junction.

7. The dental restoration structure of claim 1, wherein said cutting teeth further comprise a peripheral edge joined to said non-cutting edge by a pointed junction.

8. A dental restoration structure comprising a crown structure comprising a layer to which a tooth structure is bonded, and an integral collar comprising aligned bores and to which said layer is bonded; means for connecting said crown structure to an implant, said connecting means comprising a crown end comprising an inclined transverse bore, wherein said aligned bores of said collar form a correspondingly inclined bore for coaxial alignment with said inclined transverse bore, and said crown structure having a cavity defined by an inner peripheral wall of said collar and by said layer, said cavity having a mating interior shape and dimensions for fitting over said crown end of said connecting means.

9. The dental restoration structure of claim 8, wherein said integral collar is overlayed by said layer.

\* \* \* \* \*